United States Patent [19]

Lewis

[11] B 4,000,641
[45] Jan. 4, 1977

[54] FRICTION MEASURING APPARATUS
[75] Inventor: William Dein Lewis, Wilmington, Del.
[73] Assignee: E. I. Du Pont de Nemours and Company, Wilmington, Del.
[22] Filed: May 2, 1975
[21] Appl. No.: 573,994
[44] Published under the second Trial Voluntary Protest Program on March 23, 1976 as document No. B 573,994.
[52] U.S. Cl. .................................. 73/9; 73/160
[51] Int. Cl.² .................................. G01N 19/02
[58] Field of Search .................. 73/9, 144, 160

[56] References Cited

UNITED STATES PATENTS

| 2,378,614 | 6/1945 | Zahn | 73/9 |
|---|---|---|---|
| 3,324,719 | 6/1967 | Segrave | 73/160 |
| 3,556,369 | 1/1971 | Ferguson | 226/25 |
| 3,813,917 | 6/1974 | Cole | 73/9 |

FOREIGN PATENTS OR APPLICATIONS

| 842,919 | 7/1960 | United Kingdom | 73/9 |

Primary Examiner—S. Clement Swisher
Assistant Examiner—Frederic Shoon

[57] ABSTRACT

A portable frictometer employing the principle of passing a standard yarn sample across a cylindrical surface under test at a fixed wrap angle and detecting the ratio of the yarn tensions at the output and input ends of the wrap. This ratio is related to the coefficient of friction of the surface under test. The apparatus includes a yarn guiding system of two guide pulleys at the extremities of two rigid arms so as to achieve a predetermined fixed yarn wrap on the cylindrical surface under test when the arms are placed to contact and straddle the surface and a tension ratio monitor consisting of a disc rotatably mounted about its center with two small concentric central yarn guide pulleys and two separated peripheral guide pulleys thereon. The disc is coupled with a readout arrangement that provides a reading of the deflection of the disc which is proportional to the ratio of tensions in two yarn sections passing respectively across the peripheral pulleys and thence each around the central pulley and on to or from yarn supply reels.

5 Claims, 3 Drawing Figures

FRICTION MEASURING APPARATUS

BACKGROUND OF THE INVENTION

This invention relates to apparatus for the measurement of the coefficient of friction between a flexible elongate material such as a yarn, thread or fiber and a cylindrical surface. More particularly, this invention concerns a portable frictometer calibrated to read directly the coefficient of friction between a yarn and the outside surface of a cylindrical roll, guide or pin.

Known frictometers such as that disclosed by Seagrave in U.S. Pat. No. 3,324,719 employ mechanisms for forwarding a yarn at a controllable, predetermined rate of speed over a stationary test surface and tensiometers for measuring the input and output tensions in the yarn traversing this surface. Friction coefficients are related to tension ratios. Strain gages for tension readings are attached to pulleys over which the yarn on the input side and output side of the pin, respectively, is made to pass. Other means for measuring input and output tension of yarn passing over a surface include the use of beam balance arms on which yarn carrying pulleys are mounted such as shown in British Pat. No. 842,919. Another frictometer type comprises, as shown in U.S. Pat. No. 2,378,614 by Zahn, a mechanism for mounting the friction surface as a roll on a pivot. A counterbalance is provided on the roll so that the angular deflection of the roll is a measurement of the difference between input and output yarn tension and, therefore, friction as yarn slides over the roll surface. Still another type of tensiometer, which might be combined into a frictometer, is disclosed by Campbell in U.S. Pat. No. 2,538,932 wherein a disc is mounted on a spring biased shaft and two pulleys are provided on the disc along a diameter thereof. Yarn passing around one pulley, through the axis of the disc and around the other pulley, in an "S"-shaped path, exerts torque against the spring bias as a result of tension in the yarn. A deflection of the disc against the spring bias is a measure of the yarn tension. Ferguson in U.S. Pat. No. 3,556,369 discloses a device for regulating tension which employs similar structure.

Although these devices operate satisfactorily for many measurement situations, none provides easy portability with direct readability of coefficient of friction after a simple easily accomplished calibration. For example, no prior instrument is known which could be taken to a yarn producing location and applied to measure the coefficient of friction of the drive roll of a yarn winding apparatus without first disassembling the windup to remove or make accessible the drive roll for measurement.

SUMMARY OF THE INVENTION

This invention comprises a frictometer for measuring the coefficient of friction between a yarn and a cylindrical surface consisting of a frame having two arms extending at a fixed included angle from a central point. Two guide pulleys are mounted on frictionless bearings, one near the outer end of each arm, in such a way that the periphery of a pulley is tangent to the inner surface of each arm. A disc is mounted on a frictionless shaft through the frame along the line bisecting the angle between the arms. Two central pulleys are mounted on frictionless bearings attached to the center of this disc and two peripheral pulleys are mounted also on frictionless bearings through axes parallel to the axis of this central pulley but located near the periphery of the disc. These latter are separated by nearly one half the circumference of the disc.

Two yarn reels are mounted on shafts extending through the frame above the disc and on opposite sides of the central axis. The shafts of these reels extend through the frame to electric motors mounted on the back of the frame. A mechanism is provided for measuring the angular deflection of the disc when yarn is passed from one reel to another along a prescribed path extending first around one central pulley on the disc, then around one peripheral pulley on this disc, and to the pulley at the end of one arm. Then the yarn passes across the friction surface under investigation to and around the pulley at the end of the other arm. Thence, the yarn passes around the other peripheral pulley, around the other central pulley and up to the second reel.

The coefficient of friction between the yarn and the cylindrical roll surface is measured by noting the deflection of the disc when the device is held with the yarn extending between the two pulleys at the ends of the two arms and is pressed against the roll until the roll surface is tangent to the inner surfaces of the two arms and the yarn is driven between the two yarn reels. In this way, a fixed wrap angle of the yarn on the roll is achieved and coefficient of friction is related to the ratio of yarn input and output tensions.

DETAILED DESCRIPTION OF THE PREFERRED EMBODIMENT

Figure 1:
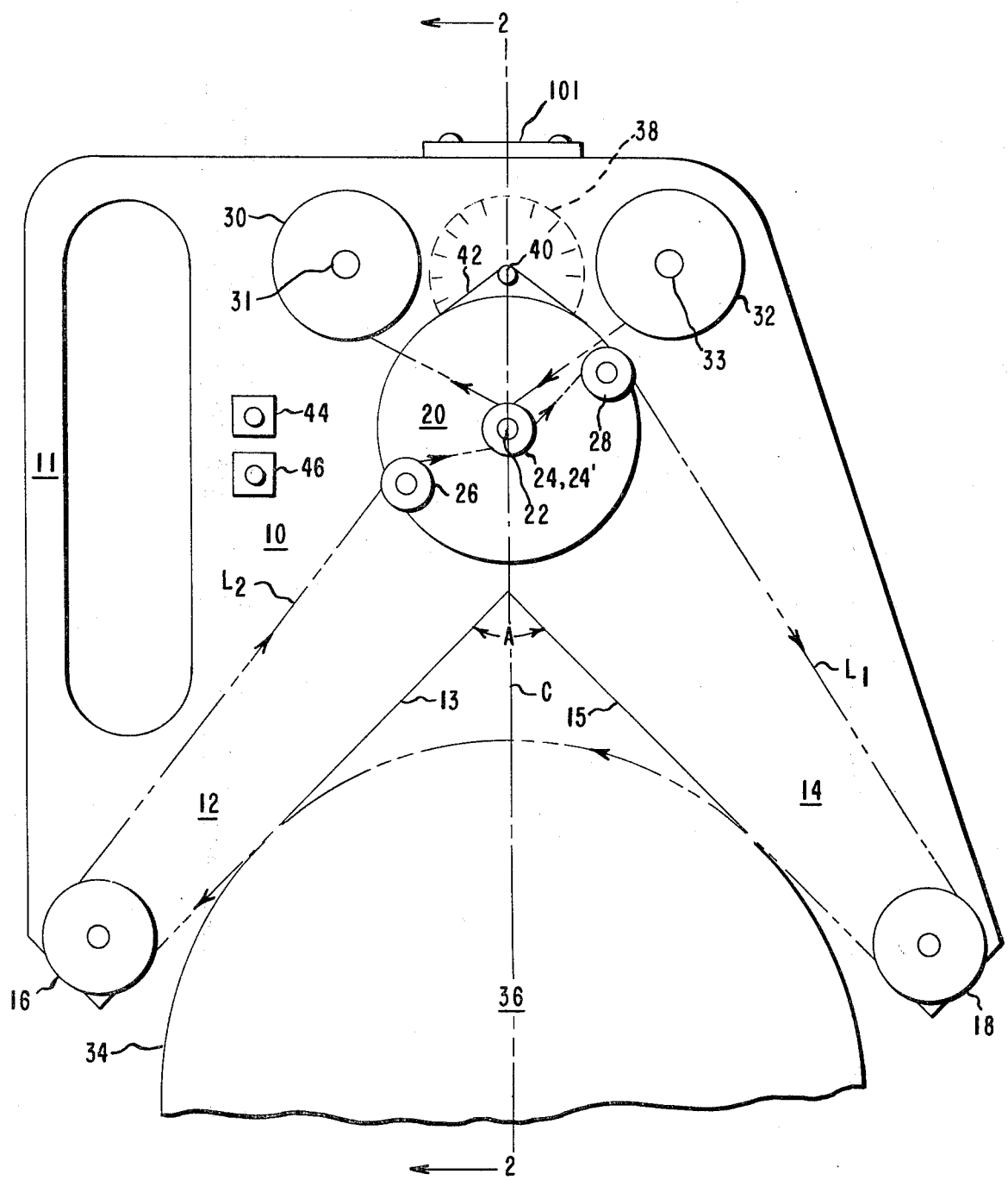
FIG. 1 is a plan view of the apparatus shown in association with a roll, the coefficient of friction of which it is being determined against a yarn.

Turning first to FIG. 1, the apparatus of this invention is seen to comprise first an irregularly shaped frame 10 having a handle portion 11 and two arms 12, 14 extending each at 45° to the bisecting center line C. A first guide pulley 16 is mounted on a frictionless shaft near the extremity of arm 12 and arranged so that its periphery is tangent to the inner surface 13 of arm 12. A second guide pulley 18 is similarly mounted on arm 14 with its periphery tangent to surface 15. The angle A between the inner surfaces 13, 15 of arms 12, 14 was selected for convenience to be 90°. However, for special purposes this angle could be selected to be a more convenient value. This angle, however, is fixed for a given embodiment in order that the calibration of the apparatus is constant.

Figure 2:
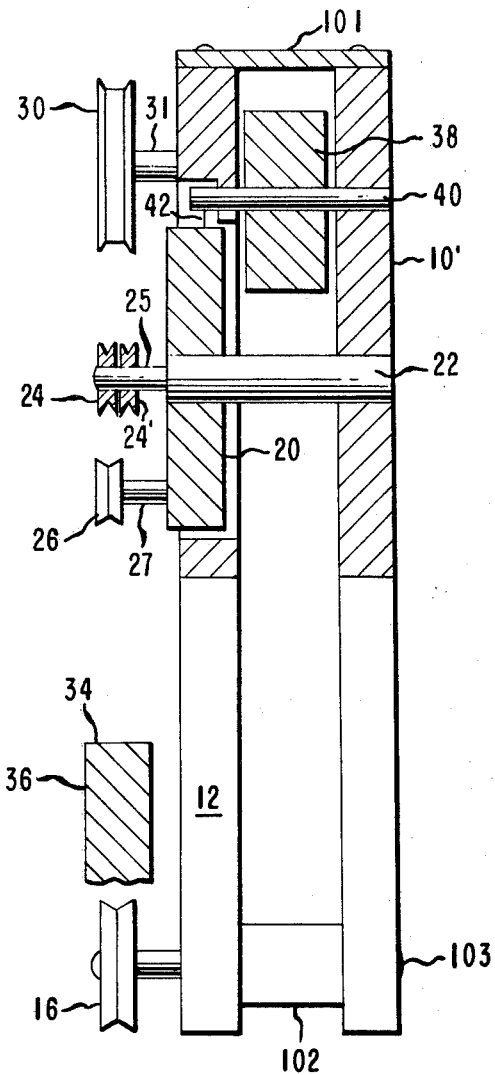
FIG. 2 is a vertical cross-sectional view of the apparatus along lines 2—2 of FIG. 1.

Continuing with FIGS. 1 and 2, a torque disc 20 is mounted in a circular recess in frame 10 on a frictionless shaft 22 which extends through frame 10 to a rear frame 10'. Frame sections 10, 10' are fastened together by means of a top plate 101 and spacers 102 and bolts 103 near the outer ends of arms 12, 14. Central pulleys 24, 24' are mounted on shaft 25 with frictionless bearings concentric with shaft 22. A first peripheral pulley 26 is mounted on shaft 27 with frictionless bearings. It is attached and extends from the front surface of disc 20 near the periphery of this disc. A second peripheral pulley 28 is similarly mounted on disc 20 at a position roughly diametrically opposite pulley 26. Two yarn reels 30, 32 are mounted above disc 20 on shafts 31 and 33 extending through frame 10 to separate electric motors (not shown) for driving reels 30, 32. These motors are conventional miniature DC electric motors. A readout drum 38 is mounted between front frame 10 and rear frame 10' on shaft 40. This shaft projects forward to receive a linking monofil loop 42 which extends around this projection on shaft 40 and around the periphery of disc 20. Drum 38 carries calibration marks which may be read against an index on the frame and thereby indicate the deflection of disc 20. Supplies of yarn are carried on reels 30, 32. This yarn is threaded, for example, from reel 30 to one central pulley 24, around pulley 26 to guide pulley 16, thence around roll surface 34 to pulley 18, up to pulley 28, around the other central pulley 24' and finally to reel 32.

Figure 3:
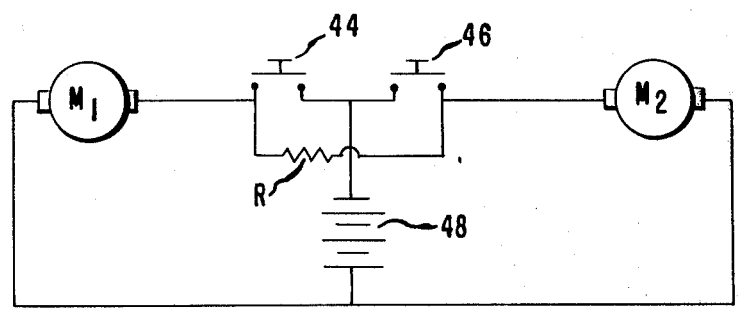
FIG. 3 is a schematic electrical circuit diagram of an exemplary arrangement for driving the motors attached to the two yarn reels.

A pair of normally open pushbutton switches 44, 46 is fixed to frame 10 near handle 11. These switches are in the circuit with the two motors which drive the yarn reels. FIG. 3 shows an exemplary circuit diagram for connecting the two yarn reel motors $M_1$ and $M_2$ with pushbuttons 44, 46, electric cells 48, and a resistor R so that $M_1$ rotates in a direction opposite from $M_2$. The resistor R provides dynamic braking to the feed motor which in turn provides relatively constant control of yarn speed and tension in such a way that backlash or overdrive of yarn between reels 30, 32 can be prevented. The circuit location of the resistor and the direction of motor rotation is determined by which switch (44 or 46) is pushed. Therefore, yarn reel 30 may be the feed roll and 32 the take-up roll or vice versa.

In operation, this invention measured the coefficient of sliding friction between a surface and a standard yarn moving from one yarn reel to the other as it passes over a cylindrical drum or rod whose outer surface is being tested. This device employs the well-known pulley or belt-friction formula; namely, $f = 1/\theta \log(T_2/T_1)$ where $f$ is the coefficient of sliding friction of the yarn over the surface, $\theta$ is the angle of wrap of the yarn over the surface, and $T_2/T_1$ is the ratio of the yarn tension as it is pulled off the surface to that as it is introduced to the surface, respectively. In the embodiment illustrated in the drawings, the angle of wrap $\theta$ is 90° since friction readings are taken when arms 12, 14 are both tangent to the test roll and since their inner surfaces 13, 15 are constructed at a 90° angle. The tensions $T_2$ and $T_1$ are respectively the tensions in yarn sections $L_1$ and $L_2$ as noted in FIG. 1 since pulleys 16, 18 are essentially frictionless.

The arrangements of disc 20 with pulleys 24, 24', 26 and 28 associated therewith and of drum 38 combine to provide a measurement of the ratio of tensions $T_2/T_1$. It is easily seen from FIG. 1 that only the tensions in lines $L_2$ and $L_1$ produce any torque on disc 20. All other lines exert no torque since they extend radially to or from the center pulleys 24, 24'. When the tensions in $L_2$ and $L_1$ are made equal, i.e., $(T_2/T_1) = 1$, such as during a zero deflection calibration, disc 20 will be so oriented that pulleys 26, 28 will lie at equal angles to the center line C. In this configuration, drum 38 will be considered at zero reading.

If the tension in $L_2$ is larger than the tension in $L_1(T_2/T_1 > 1)$, the disc will be rotated slightly counterclockwise as shown in exaggerated form in FIG. 1. This is the situation when coefficient of friction is being measured with yarn running in direction of arrows, i.e., from reel 32 to reel 30. The deflection of disc 20 and, therefore, the reading on drum 38 can be shown from the geometry of the apparatus to be linearly related to the ratio $T_2/T_1$. Thus, the markings on drum 38 can be made to read in units of coefficient of friction between the yarn and the surface 34 of drum 36 by virtue of the above-noted belt formula.

Calibration of the device, as mentioned above, may easily be carried out by taking a loop of yarn, winding it once around central pulleys 24, 24' and then bring the two ends respectively around pulleys 26 and 28 and pulleys 16 and 18. Equal masses are then placed on each of the yarn ends as they hang below pulleys 16 and 18 while the device is held in a vertical plane. This arrangement as noted will provide the zero reading on readout drum 38.

Many advantages for this invention include not only portability, along with ease of operation and calibration but also insensitivity to whether the device is held vertical, horizontal or in between.

While two separately mounted central pulleys 24, 24' are preferred to accommodate yarn stretch, a single pulley with either a single or a double groove may be substituted in their place.

Further modifications will be apparent to one skilled in the art. The provision of a more sophisticated readout arrangement than drum 38 is possible such as by substitution of a digital readout counter. It is also evident that the device may be used to determine static friction between a yarn and a drum surface by clamping yarn reels 30, 32 and noting the maximum reading on drum 38 just prior to slipping as the device is manually pushed in a circumferential direction on the drum 36. Alternatively, the device could be held fixed, reels 30, 32 clamped and the drum 36 torqued until maximum reading is obtained on drum 38. Similarly, sliding friction could be determined by clamping reels 30, 32 and rotating drum 36 to provide a reading on drum 38. However, it is considered more reliable when determining the coefficient of friction of a drum surface to provide fresh yarn by driving yarn between reels 30, 32 while drum 36 is stationary. Furthermore, it is convenient to provide substitute reels of yarn of different kinds which may be put in place of reels 30, 32 to provide friction values for different types of yarns or yarn finish compositions.

What is claimed is:

1. An apparatus for measuring friction between a yarn and a cylindrical surface comprising:
   a frame having two arms extending outwardly at a fixed included angle from a common central location on a line bisecting the angle, said arms each having an inner surface for resting on said cylindrical surface;
   a pulley rotatably mounted at the end of each of said arms, each pulley having a peripheral surface tangent to said inner surface of its associated arm;
   a disc rotatably mounted at its center on a fixed pivot on said frame at a location above said arms on said line bisecting said angle, said disc having at least one yarn pulley rotatably mounted thereon at said pivot and two other yarn pulleys mounted rotatably thereon near the periphery of said disc, said two other yarn pulleys being separated by substantially one-half the circumference of said disc;

two driven yarn supply reels mounted on said frame above said fixed pivot on opposite sides of said line bisecting said angle;

means for driving said reels; and means for sensing the angular position of said disc with respect to said frame when yarn is passed across said cylindrical surface in a prescribed path around said pulleys from one supply reel to the other.

2. The apparatus of claim 1, said fixed angle being 90°.

3. The apparatus of claim 1, there being two separate rotatably mounted pulleys on said disc at said pivot.

4. The apparatus of claim 1, said prescribed path being the yarn path passing from one reel around the yarn pulley in the center of the disc, then around one yarn pulley on the periphery of the disc, then around the pulley at the end of one arm and across said cylindrical surface to the pulley at the end of other arm, then around the other yarn pulley on the periphery of the disc, then back around the pulley in the center of the disc and on to the other reel.

5. The apparatus of claim 1, the means for driving said reels comprising: a pair of motors, one for each reel; a source of DC power; and means connected between said motors and said source for dynamically braking one motor with respect to the other.

* * * * *